(12) United States Patent
Wang et al.

(10) Patent No.: US 11,970,747 B2
(45) Date of Patent: Apr. 30, 2024

(54) PRIMER-PROBE COMBINATION AND KIT FOR VAGINAL MICROECOSYSTEM DETECTION

(71) Applicant: BEIJING ORIGIN-POLY BIO-TEC CO., LTD., Beijing (CN)

(72) Inventors: Linhai Wang, Beijing (CN); Pei Liu, Beijing (CN)

(73) Assignee: BEIJING ORIGIN-POLY BIO-TEC CO., LTD., Beijing (CN)

( * ) Notice: Subject to any disclaimer, the term of this patent is extended or adjusted under 35 U.S.C. 154(b) by 0 days.

(21) Appl. No.: 18/152,554

(22) Filed: Jan. 10, 2023

(65) Prior Publication Data

US 2023/0332250 A1    Oct. 19, 2023

Related U.S. Application Data

(63) Continuation of application No. PCT/CN2022/128559, filed on Oct. 31, 2022.

(30) Foreign Application Priority Data

Apr. 18, 2022    (CN) .......................... 202210402142.5

(51) Int. Cl.
  *C12Q 1/689*    (2018.01)
  *C12Q 1/6806*   (2018.01)
  *C12Q 1/6816*   (2018.01)

(52) U.S. Cl.
  CPC .......... *C12Q 1/689* (2013.01); *C12Q 1/6806* (2013.01); *C12Q 1/6816* (2013.01); *C12Q 2600/16* (2013.01)

(58) Field of Classification Search
  CPC .... C12Q 1/689; C12Q 1/6806; C12Q 1/6816; C12Q 2600/16
  See application file for complete search history.

(56) References Cited

U.S. PATENT DOCUMENTS

| | | | |
|---|---|---|---|
| 2013/0316922 | A1 | 11/2013 | Balashov |
| 2018/0291430 | A1 | 10/2018 | Eaton |

FOREIGN PATENT DOCUMENTS

| | | | |
|---|---|---|---|
| CN | 102719529 | A | 10/2012 |
| CN | 110343780 | A | 10/2019 |
| CN | 112176079 | A | 1/2021 |
| CN | 112301169 | A | 2/2021 |
| WO | 2008062136 | A2 | 5/2008 |
| WO | 2016020081 | A1 | 2/2016 |

OTHER PUBLICATIONS

Dumonceaux et al., Journal of Clinical Microbiology, 47(12), 4067-4077, Dec. (Year: 2009).*

* cited by examiner

*Primary Examiner* — Cynthia B Wilder
(74) *Attorney, Agent, or Firm* — NIXON PEABODY LLP; Mark J. Fitzgerald; Alissa R. Young

(57) ABSTRACT

Disclosed in the present invention are a primer-probe combination and a kit for vaginal microecosystem detection, wherein the primer-probe combination comprises primers and probes for target gene detection against *Lactobacillus crispatus* (LC), *Lactobacillus gasseri* (LG), *Lactobacillus jensenii* (LJ), *Lactobacillus iners* (LI), *Gardnerella vaginalis* (GV), *Candida albicans* (CA) and *Trichomonas vaginalis* (TV), and the probes are used for melting curve analysis. The kit comprises the primer-probe combination. The combination of specific primers and probes enables effective amplification of specific target genes of the above different microorganisms and melting curve analysis performed on the amplified products thereof, making detection of the above seven microorganisms in a single tube possible, thus achieving the advantages of high specificity, short time consuming, high sensitivity, comprehensive coverage of detection sites, etc., which provides clinicians with auxiliary diagnosis reference, ensures early treatment, and has wide clinical application.

5 Claims, 1 Drawing Sheet

Specification includes a Sequence Listing.

PRIMER-PROBE COMBINATION AND KIT FOR VAGINAL MICROECOSYSTEM DETECTION

CROSS REFERENCE TO RELATED APPLICATIONS

This application claims benefit to International Application No. PCT/CN2022/128559 filed on Oct. 31, 2022, which claims benefit under 35 U.S.C. § 119(b) of CN Application No. 202210402142.5 filed on Apr. 18, 2022, the contents of both of which are incorporated herein by reference in their entireties.

SEQUENCE LISTING

The instant application contains a Sequence Listing which has been submitted electronically in .XML format and is hereby incorporated by reference in its entirety. Said XML copy, created on Jan. 6, 2023, is named 070019-000102USC1_SL.xml and is 73,437 bytes in size.

TECHNICAL FIELD

The present invention relates to the technical field of gene detection, in particular to a primer set and a kit for vaginal microecosystem balance risk detection.

BACKGROUND ART

The female vagina internal environment refers to the micro-ecological environment formed by all the microbiota residing in the female vaginal cavity. Under normal circumstances, a large number of microorganisms reside in the female vaginal cavity, and these microorganisms play an important role in the local microenvironment and maintain the healthy state of the female vagina. Studies have proved that there are significant differences in vaginal microorganisms among female of different ages. Before puberty, female vaginal microbiota is typically characterized by low-abundance *Lactobacillus*, *Gardnerella vaginalis* and *Prevotella bivia*. With the beginning of puberty, under the stimulation of estrogen, vaginal epithelium thickens again, which is beneficial to the colonization of glucose-fermenting bacteria in vagina. The vaginal microbiota of adolescent female is similar to that of adult female, and mainly consists of *Lactobacillus* crispatus, *Lactobacillus* gasseri, *Lactobacillus* iners and *Lactobacillus* jensenii. *Lactobacillus* is the main dominant bacterium in the vaginal microbiota of female of childbearing age, in which there are also a small amount of other anaerobic bacteria. *Lactobacillus* can maintain the weakly acidic environment of vagina by producing acids and hydrogen peroxide ($H_2O_2$), thus inhibiting the growth of pathogenic bacteria and maintaining the normal internal environment of vagina. When the abundance of *Lactobacillus* in vagina decreases or the function of *Lactobacillus* decreases, other anaerobic bacteria in vagina proliferate excessively, which leads to the imbalance of vaginal microecosystem and the disorder of internal environment, resulting in easier colonization of foreign pathogens in the female reproductive tract which can lead to local inflammation and even cancer. What's more, local pathogen infection of the vagina may increase risks of pelvic inflammatory disease, premature delivery, abortion, etc.

In 2011, Ravel studied the vaginal microbiota of 396 asymptomatic female of childbearing age, and found that the female vaginal microbiota can be divided into five types, among which *Lactobacillus* is the dominant bacterium in types 1-4, with *Lactobacillus* crispatus, *Lactobacillus* gasseri, *Lactobacillus* jensenii and *Lactobacillus* iners being the dominant bacteria, respectively, while in type 5, the microbiota is diversified, with no dominant bacteria, reduced proportion of *Lactobacillus* and significantly increased proportion of anaerobic bacteria. Among these five types, the first three with higher proportions are: the type with *Lactobacillus* crispatus as the dominant bacterium, the type with *Lactobacillus* iners as the dominant bacterium, and the type with no dominant bacteria. Studies have also shown that there is a type dominated by both *Lactobacillus* crispatus and *Lactobacillus* iners. The imbalance of vaginal microecosystem is mainly due to the reduction of *Lactobacillus* and the loss of its dominant position. Bacterial vaginosis (BV) (mainly *Gardnerella vaginalis*), trichomonal vaginitis (TV), vulvovaginal candidiasis (VVC, also referred to as candidiasis) and aerobic vaginitis (AV) are relatively common. Among them, mixed vaginitis has gradually been paid more and more attention by gynecology in study in recent 10 years. In a patient with mixed vaginitis, the vaginal microecological balance is severely damaged, and the microecological manifestations are more complex and diverse, making diagnosis and treatment more difficult than those of single vaginal infection. In addition, if mixed infection is not found, diagnosed and treated in time, risks of treatment failure and repeated attacks of infection will be higher.

The relapse of vaginitis also leads to considerable economic losses. In 2018, Lancet literature reported that in high-income countries, the loss of productivity caused by the relapse of VVC can bring about an annual economic burden of up to $1.439 billion. Therefore, a comprehensive and correct understanding of vaginitis, especially mixed vaginitis, and vaginal microecosystem is helpful to the correct diagnosis and reasonable treatment of vaginal inflammation, and is of great significance to prevention of the relapse of mixed infection, improvement of the female vaginal microecosystem, etc. Therefore, it is necessary to have a clear identification of the types of vaginal microorganisms, so as to significantly distinguish the types of microorganisms that cause vaginitis infection. Currently, there is no corresponding detection product available on the market to meet the clinical needs.

SUMMARY OF THE INVENTION

The objective of the present invention is to provide a detection primer-probe combination and a kit capable of accurately distinguishing between different vaginal microorganisms, which makes possible the detection of multiple vaginal microorganisms in a single tube only by a conventional fluorescent quantitative PCR instrument.

The technical solutions of the present invention are described in detail as follows:

In a first aspect, the present invention provides a primer-probe combination for vaginal microecosystem detection suitable for high-resolution melting curve analysis, comprising primers and probes for target gene detection against *Lactobacillus* crispatus (LC), *Lactobacillus* gasseri (LG), *Lactobacillus* jensenii (LJ), *Lactobacillus* iners (LI), *Gardnerella vaginalis* (GV), *Candida albicans* (CA) and *Trichomonas vaginalis* (TV), wherein the nucleotide sequences of the probes are labeled with fluorophores at the 5' end and quenching groups at the 3' end.

Optionally or preferably, the above primer-probe combination further comprises primers and probes for detection of an internal reference gene GAPDH, wherein the GAPDH detection probe is labeled with a fluorophore at the 5' end, and the fluorophore is different from that labeled at the 5' end of the probes for target gene detection.

In a second aspect, the present invention provides a kit for vaginal microecosystem detection, comprising the primer-probe combination described above.

Optionally or preferably, the above kit further comprises a PCR reaction solution, wherein each one-person-portion of the PCR reaction solution is composed of 0.5-1 μL of Taq DNA polymerase multi-amplified at a concentration of 1 U/μL, 1-5 μL of dNTPs at a concentration of 10 mM, 2-5 μL of $Mg^{2+}$ at a concentration of 5 mM, 2.5 μL of 10×DNA polymerase buffer and purified water making up to 15 μL.

Optionally or preferably, the above kit further comprises a cell lysate composed of, by mass percentage, 1% TritonX-100™ detergent, 0.1% SDS, 1% sodium deoxycholate, 1% NP-40™ detergent, and the balance of purified water.

The melting temperature (Tm) value is the temperature at which primers and templates complement each other accurately, and when templates are excessive, 50% of the primers are paired with the templates, while the other 50% of the primers are in a dissociated state.

High-resolution melting (HRM) curve analysis is a gene analysis based on the fact that melting curves of different morphology are formed due to different melting temperatures of single nucleotides. The saturated fluorescent dye emits fluorescence when being combined with DNA double strands, and the fluorescence signal decreases drastically when released from the DNA double strands. A melting curve is obtained by denaturing the DNA with elevated temperature and plotting the fluorescence signal with the temperature as the x-coordinate.

Compared with the prior art, the present invention has the following beneficial effects:

In the present invention, primers and probes are combined to improve the detection specificity. The primers designed can match the unique target gene of each microorganism, have a sequence with the 5' end having a sequence of 3-5 bp in length which is complementary to and paired with the 3' end to form a hairpin structure, and have a locked nucleotide modification base, making the Tm values of the primers 2-3° C. higher than the annealing temperature of a PCR reaction system and resulting in improvement of the amplification specificity. During detection, the target genes of different microorganisms are amplified using specific primers at first; however, if the amplified products are directly combined with saturated fluorescent dyes, the fluorescent dyes will be combined with the amplified products of all microorganisms, which makes distinguishing between different microorganisms by melting curves impossible. Therefore, the detection probes with specific Tm values are added, so that the amplified products can specifically bind to different types of microorganisms, thereby distinguishing between different microorganisms by melting curves. The probes designed will generate a characteristic peak (Tm value, the temperature at which 50% of DNA double strands melt) when hybridizing with and separating from the PCR amplification product templates during the generation of the melting curves, and therefore, the Tm values of the probes can be used for any one or more detections of the amplified products of target genes of microorganisms. An accurate detection can be achieved regardless of single infection or mixed infection of the vagina. Especially for mixed infection, which is relatively common clinically and displays an upward trend in recent years, clear identification can provide an important reference for clinical treatment, so as to ensure timely treatment and reduce relapse frequency.

The primer sequence provided by the present invention employs a special clasp design structure and a locked nucleic acid modification form, thereby enhancing the capture efficiency against the template sequence and the sensitivity and specificity of the PCR amplification system, and reducing the detection error. Especially for vaginal swabs as samples and the extraction-free form, the amount of DNA is small, so it is essential to improve the sensitivity. The primer sequence of the present invention enables an increase of the capture efficiency against templates in DNA, and obtaining accurate detection results with a small amount of samples, making it more suitable for clinical application.

The probe sequence provided by the present invention is mainly used for typing (distinguishing between) different target genes, and seven different vaginal microorganisms can be typed by using different Tm value distributions in the same fluorescent channel. The main design lies in using MGB modification and locked nucleic acid modification to improve Tm values and increase the hybridization efficiency between the probe and the template. With the technical solutions of the present invention, the multi-gene locus detection can be completed in batches; the detection method is simple to operate and intuitive to interpret; and results can be obtained within 3 hours. All the universal fluorescent quantitative PCR instruments can meet the detection requirements, and the experimental process adopts a one-stop fully closed form, which makes the operation simpler and the possibility of cross-contamination avoided.

The kit provided by the present invention comprises a special cell lysate, which can perform strong cell sample lysis on vaginal swabs or exfoliated cervical cells, so as to accelerate the release of genomes from cells and meet the needs of subsequent PCR amplification. In this way, the sample can be obtained in an extraction-free way during detection, and can be processed in 5 minutes, so that the sample can be directly used in the subsequent melting curve experiment using PCR-taqman probes.

DETAILED DESCRIPTION OF EMBODIMENTS

Figure 1:
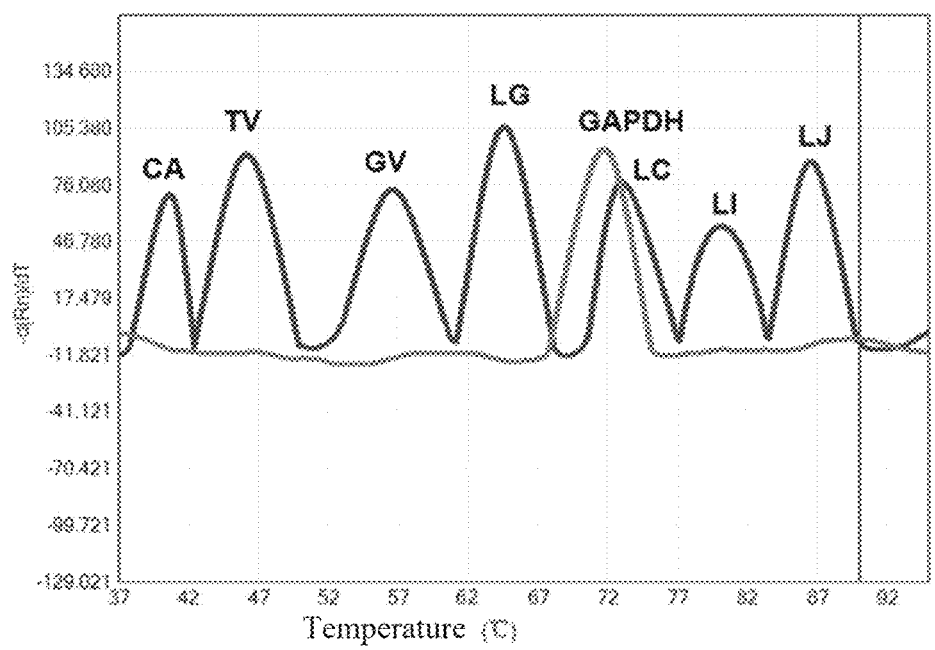
FIG. 1 is a graph showing the melting curve distribution of seven microorganisms and an internal reference gene.

The technical solutions of the present invention will be explained and described in detail below in conjunction with the accompanying drawings and the preferred specific examples, so that those skilled in the art can better understand and implement the present invention. Unless otherwise specified, the instruments and reagents used in the examples are conventional ones in the field.

Example 1 Determination of Cutoff Values of Vaginal Microorganism Compositions

The known gene sequences of *Lactobacillus* crispatus (LC), *Lactobacillus gasseri* (LG), *Lactobacillus jensenii* (LJ), *Lactobacillus iners* (LI), *Gardnerella vaginalis* (GV), *Candida albicans* (CA) and *Trichomonas vaginalis* (TV) were compared and analyzed to obtain their respective differential gene sequences. Detection primers and probes were designed for the differential gene sequences, with detection primers and probes for an internal reference gene GAPDH added in the design.

The specific nucleotide sequences of the primers designed are shown in the following table:

TABLE 1

Sequences of detection primers corresponding to target genes of microorganisms

| Primer name | Primer sequence | Primer number |
|---|---|---|
| LC-F | ctttcGGT + A + A + T + GACGTTAGGAAAG | SEQ ID NO: 1 |
| LC-R | aatacGCTTT + C + T + T + ATCCGGTATT | SEQ ID NO: 2 |
| LG-F | gtgtT + GA + C + CT + GGGCTACAC | SEQ ID NO: 4 |
| LG-R | cctTC + CAGCTTC + GTGTAGG | SEQ ID NO: 5 |
| LJ-F | gaaaCCACCTAAGA + G + ATTAGGTTTTC | SEQ ID NO: 7 |
| LJ-R | cagcGAGTGC + CCAACTTAATGCTG | SEQ ID NO: 8 |
| LI-F | ccctGCGTG + AGT + GAAGAAGGG | SEQ ID NO: 10 |
| LI-R | gcaGTATTA + CC + GCGGCTGC | SEQ ID NO: 11 |
| GV-F | gccacGGT + TG + GTGAGAGTGGC | SEQ ID NO: 13 |
| GV-R | tgctCGTCAA + G + T + T + GGAGCA | SEQ ID NO: 14 |
| CA-F | ccgcTAGG + TGA + ACCTGCGG | SEQ ID NO: 16 |
| CA-R | gaaCCA + AAG + CA + AGTTTGTTTC | SEQ ID NO: 17 |
| TV-F | gagGG + C + CACATGAATGACTC | SEQ ID NO: 19 |
| TV-R | ggggTG + AG + ATA + GATCTACCCC | SEQ ID NO: 20 |
| G-F | AAGGGTGCAGCTGAGCTAG | SEQ ID NO: 22 |
| G-R | GCACAAGCTTTGTACATGG | SEQ ID NO: 23 |

Note:
F represents a forward detection primer; R represents a reverse detection primer; and G represents an internal reference gene GAPDH.

The above primers have a sequence with the 5' end having a sequence of 3-5 bp in length which is complementary to and paired with the 3' end to form a hairpin structure, making the Tm values of the primers 2-3° C. higher than the annealing temperature of a PCR reaction system. In the annealing process, it is preferred for the primer sequence to keep its own clasp structure without forming double strands with other primers, so that no primer dimers will be formed, which ensures that the amplification between different target gene detection primers will not cause interference, and there is an obvious advantage for the amplification of multiple primers. In addition, the primer with a clasp structure has high specificity, because the binding free energy ΔG of the detection primer to the nucleotide sequence of the methylated region of the target gene is greater than the free energy ΔG of the hairpin formed by the primer itself by 3-5 kcal mol$^{-1}$.

Because the sequence homology among different vaginal microorganisms is relatively high, high specificity binding is needed to better distinguish between different types of microorganisms. Therefore, the above primer sequence also has a locked nucleic acid modification base, which is beneficial to increase the binding free energy of the detection primer to the target gene sequence template by 10-20ΔGkcal mol$^{-1}$, resulting in improvement of the capture efficiency of the primer and the target gene template, and increase of the detection sensitivity.

TABLE 2

Sequences of detection probes corresponding to target genes and Tm values

| Probe name | Probe sequence | Probe number | Tm value |
|---|---|---|---|
| LC-FP | FAM-CGG + CGGATGGG + TGAGTAA-MGB | SEQ ID NO: 3 | Tm = 74 |
| LG-FP | FAM-TGGA + CGG + TAC + AACGAG-MGB | SEQ ID NO: 6 | Tm = 64 |
| LJ-FP | FAM-CGG + G + GA + CAA + A + GAGACAGGTGG-MGB | SEQ ID NO: 9 | Tm = 86 |
| LI-FP | FAM-GCTCT + GT + T + GT + T + G + GTGAAGAAG-MGB | SEQ ID NO: 12 | Tm = 80 |
| GV-FP | FAM-TGCG + TGACCAACCT-MGB | SEQ ID NO: 15 | Tm = 57 |
| CA-FP | FAM-A + CT + G + A + TTT + GGT-MGB | SEQ ID NO: 18 | Tm = 40 |

TABLE 2-continued

Sequences of detection probes corresponding to target genes and Tm values

| Probe name | Probe sequence | Probe number | Tm value |
|---|---|---|---|
| TV-FP | FAM-CA + GT + AT + GA + AGT + CTT-MGB | SEQ ID NO: 21 | Tm = 46 |
| G-FP | HEX-CAGCAAGCATTCCTGGGGTGGC-BHQ1 | SEQ ID NO: 24 | Tm = 72 |

Note:
FP represents a detection primer, and G represents an internal reference gene GAPDH.

In this table, the probe sequences as shown have been labeled with fluorophores and quenching groups, and the probes indicate the specific Tm values for melting curves. The probes for target gene detection will generate a characteristic peak (Tm value, the temperature at which 50% of DNA double strands melt) when hybridizing with and separating from the PCR product templates during the generation of the melting curves, and therefore, the Tm values of the probes can be used for any one or more detections of different microorganisms. The above probe set includes FAM and HEX fluorescent channels, wherein the FAM fluorescent channel comprises Lactobacillus crispatus (LC), Lactobacillus gasseri (LG), Lactobacillus jensenii (LJ), Lactobacillus iners (LI), Gardnerella vaginalis (GV), Candida albicans (CA) and Trichomonas vaginalis (TV), and the HEX fluorescent channel comprises an internal reference gene. The Tm values of detection primers for the above seven vaginal microorganisms are distributed between 37-90° C., and they do not interfere with each other, and thus, the seven vaginal microorganisms, i.e., Lactobacillus crispatus (LC), Lactobacillus gasseri (LG), Lactobacillus jensenii (LJ), Lactobacillus iners (LI), Gardnerella vaginalis (GV), Candida albicans (CA) and Trichomonas vaginalis (TV) can be distinguished in the FAM channel between 37-90° C.

Table 3. Sequences of target genes of microorganisms and of an internal reference gene corresponding to primers and probes

TABLE 3

Sequences of target genes of microorganisms and of an internal reference gene corresponding to primers and probes

| Microorganism | Target gene sequence | Target gene number |
|---|---|---|
| LC | GGTAATGACGTTAGGAAAGCGAGCGGCGGATGGGTGAGTAACACGTGGGGAACCTGCCCCATAGTCTGGGATACCACTTGGAAACAGGTGCTAATACCGGATAAGAAAGC | SEQ ID NO: 25 |
| LG | TGACCTGGGCTACACACGTGCTACAATGGACGGTACAACGAGAAGCGAACCTGCGAAGGCAAGCGGATCTCTGAAAGCCGTTCTCAGTTCGGACTGTAGGCTGCAACTCGCCTACACGAAGCTGGA | SEQ ID NO: 26 |
| LJ | CCACCTAAGAGATTAGGTTTTCCCTTCGGGGACAAAGAGACAGGTGGTGCATGGCTGTCGTCAGCTCGTGTCGTGAGATGTTGGGTTAAGTCCCGCAACGAGCGCAACCCTTGTTAATAGTTGCCAGCATTAAGTTGGGCACTC | SEQ ID NO: 27 |
| LI | GCGTGAGTGAAGAAGGGTTTCGGCTCGTAAAGCTCTGTTGTTGGTGAAGAAGGACAGGGGTAGTAACTGACCTTTGTTTGACGGTAATCAATTAGAAAGTCACGGCTAACTACGTGCCAGCAGCCGCGGTAATAC | SEQ ID NO: 28 |
| GV | GGTTGGTGAGAGTGGCGAACGGGTGAGTAATGCGTGACCAACCTGCCCCATGCTCCAGAATAGCTCTTGGAAACGGGTGGTAATGCTGGATGCTCCAACTTGACG | SEQ ID NO: 29 |
| CA | TAGGTGAACCTGCGGAAGGATCATTACTGATTTGGTGAATTGCACCACATGTGTTTTTCTTTGAAACAAACTTGCTTTGG | SEQ ID NO: 30 |
| TV | GGCCACATGAATGACTCAGCGCAGTATGAAGTCTTTGTTTTCTTCCGAAAACAAGCTCAATGAGAGCCATCGGGGGTAGATCTATCTCA | SEQ ID NO: 31 |
| GAPDH | AAGGGTGCAGCTGAGCTAGGCAGCAGCAAGCATTCCTGGGGTGGCATAGTGGGGTGGTGAATACCATGTACAAAGCTTGTGC | SEQ ID NO: 32 |

Using the primers and probes listed in the above Table 1 and Table 2, a detection kit (PCR amplification system kit) was prepared, the detection kit comprising a PCR reaction solution, a mixture solution of primers and probes, a positive quality control product and a negative quality control product, and the components are listed in Table 4 below:

TABLE 4

Composition of a PCR amplification system kit

| Component | Main ingredient |
|---|---|
| PCR reaction solution | 0.5-1 μL of Taq DNA polymerase at a concentration of 1 U/μL; 1-5 μL of dNTPs at a concentration of 10 mM; 2-5 μL of $Mg^{2+}$ at a concentration of 5 mM; 2.5 μL of 10 × DNA polymerase buffer; Purified water making up to 12.5 μL. |
| Mixed solution of primers and probes | Forward and reverse primers and probes of LC gene, forward and reverse primers and probes of LG gene, forward and reverse primers and probes of LJ gene, forward and reverse primers and probes of LI gene, forward and reverse primers and probes of GV gene, forward and reverse primers and probes of CA gene, forward and reverse primers and probes of TV gene, and primers and probes of GAPDH gene. |
| Positive quality control product | DNA fragments of seven vaginal microorganisms and the internal reference gene |
| Negative quality control product | Purified water |

80 vaginal swab samples of known types of *Lactobacillus crispatus* (LC), *Lactobacillus gasseri* (LG), *Lactobacillus jensenii* (LJ), *Lactobacillus iners* (LI), *Gardnerella vaginalis* (GV), *Candida albicans* (CA) and *Trichomonas vaginalis* (TV) were selected (including samples infected by two or three vaginal microorganisms or coexisting with *Lactobacillus*, such as GV+CA, GV+TV, GV+CA+TV, LI+GV+CA, LI+GV+TV and other types), and 80 vaginal swab samples without the aforementioned types of vaginal microorganisms were further selected. The typing of the above samples was compared by the culture method and Nugent score as the gold standard reference.

I. Methylation Pretreatment for Samples

The cell lysate was first formulated, which was composed of purified water, and by mass percentage, 1% TritonX-100™ detergent, 0.1% SDS, 1% sodium deoxycholate, and 1% NP-40™ detergent. To the above vaginal swab samples was added 100 μL of cell lysate, and the mixture was kept at 90° C. for 5 minutes for use by the subsequent PCR amplification templates.

II. Melting Curve Experiment Using PCR-Taqman Probes

1. Formulation of a PCR Reaction Solution and a Mixed Solution of Primers and Probes

TABLE 5

PCR reaction solution (15 μL/person)

| Component | Adding amount/person (μL) |
|---|---|
| Taq DNA polymerase | 1 |
| dNTPs (10 mM) | 3 |
| $Mg^{2+}$ (2-5 mM) | 5 |
| 10 × DNA polymerase buffer | 2.5 |
| Purified water | Making up to 15 μL |

In the above PCR reaction system, the Taq DNA polymerase has a strong amplification capacity for multiple gene primers and probes, and the proportion of dNTPs, $Mg^{2+}$, and 10×DNA polymerase buffer also directly affects the amplification efficiency of the primer-probe combination.

TABLE 6

Mixed solution of primers and probes (5 μL/person)

| Component | Adding amount/person (μL) |
|---|---|
| LC/LG/LJ/LI/GV/CA/TV-F (100 μM) | 0.01-0.05 |
| LC/LG/LJ/LI/GV/CA/TV-R (100 μM) | 0.03-0.075 |
| LC/LG/LJ/LI/GV/CA/TV-FP (100 μM) | 0.05-0.075 |
| GAPDH gene-F (100 μM) | 0.05 |
| GAPDH gene-R (100 μM) | 0.05 |
| GAPDH gene-FP (100 μM) | 0.05 |
| Purified water | Making up to 5 μL |

2. Addition of Samples

5 μL of negative quality control product, positive quality control product and clinical sample templates in the step 1 were respectively added to the above formulated system. PCR amplification reaction was performed. 3. The amplification procedure is as follows:
  step 1: pre-denaturation at 95° C. for 3 min;
  step 2: denaturation at 94° C. for 15 s, annealing and extension at 60° C. for 45 s, 50 cycles;
  step 3: at 25° C. for 1 min;
2. Melting Curve Conditions Using Taqman Probes
  step 1: pre-denaturation at 95° C. for 3 min;
  step 2: at 37° C. for 3 min;
  step 3: from 37° C. up to 90° C. at a temperature increasing rate of 0.1° C./s (fluorescence collection);
  step 4: at 25° C. for 1 min;
  Note: For signal collection, FAM and HEX fluorescence signals were collected.
5. Analysis of Detection Results 160 negative and positive control samples of each vaginal microorganism type were analyzed separately, and the cutoff value of each vaginal microorganism was determined by the ROC curves, including the range of Tm values and −d(Rn)/dT (the peak value of melting peak on the y-coordinate).

Note: The 160 negative and positive control samples refer to 80 negative and 80 positive samples of a certain microorganism selected from many samples, and the total number of positive samples of this type of microorganism is 80. The separate analysis means that the microorganism types contained in a sample are calculated separately. For example, when a sample contains three types of LC, LG and LJ, the sample is considered a positive control for the calculation of the LC, a positive control for the calculation of the LG and also a positive control for the calculation of the LJ, and can be considered a negative control for the calculation of the CA, TV and other microorganism types.

The statistical analysis by the ROC curves is shown in the following table:

TABLE 7

Threshold values to interpret vaginal microorganisms

| Type of vaginal microorganism | Channel | Tm value | −d(Rn)/dT |
|---|---|---|---|
| *Lactobacillus crispatus* (LC) | FAM | 72.36-75.84 | ≥24.32 |
| *Lactobacillus gasseri* (LG) |  | 63.35-64.96 | ≥29.94 |
| *Lactobacillus jensenii* (LJ) |  | 84.41-88.22 | ≥12.00 |
| *Lactobacillus iners* (LI) |  | 78.65-80.75 | ≥33.15 |
| *Gardnerella vaginalis* (GV) |  | 55.23-58.73 | ≥12.12 |
| *Candida albicans* (CA) |  | 38.26-41.85 | ≥19.14 |
| *Trichomonas vaginalis* (TV) |  | 44.37-47.16 | ≥15.61 |
| Internal reference gene (GAPDH) | HEX | 71.02-73.28 | ≥10.28 |

Figure 2:
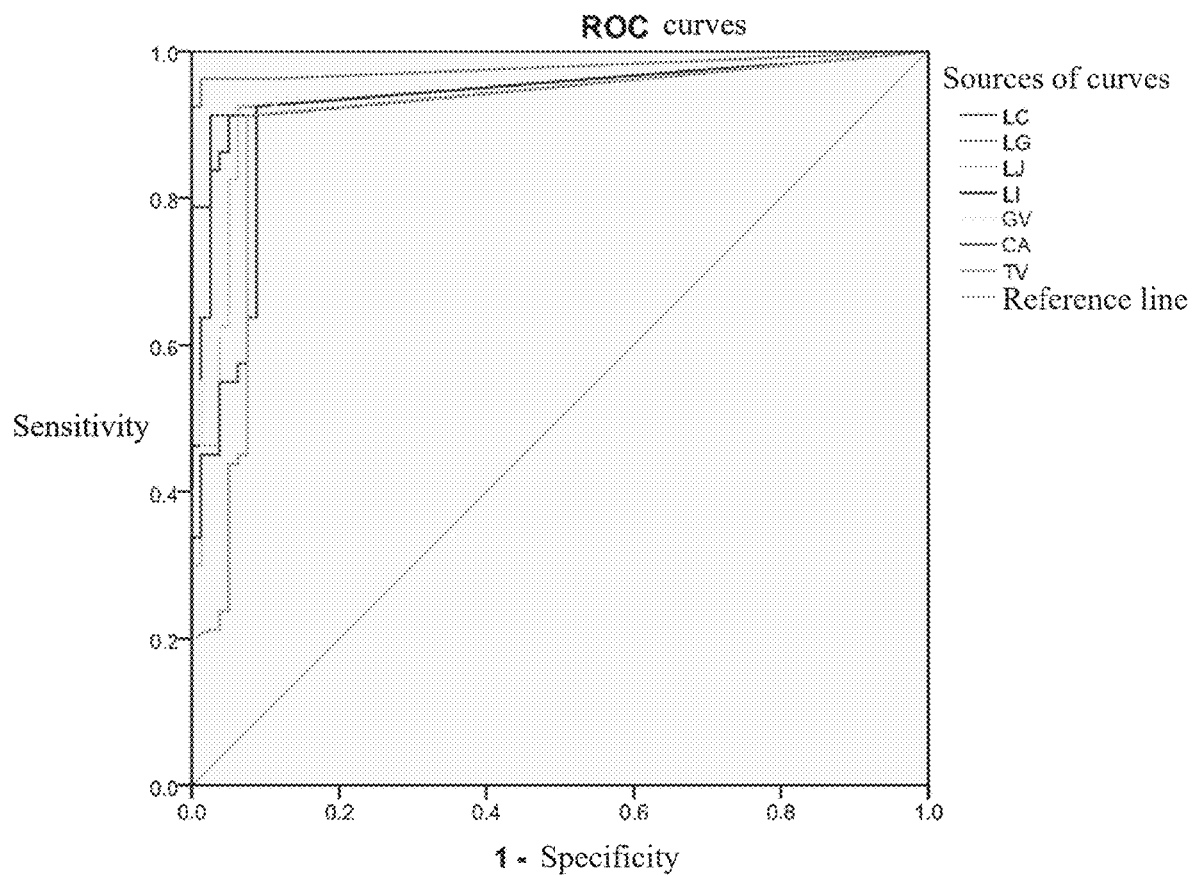
FIG. 2 is a graph showing the ROC curves for detection of seven microorganisms.

The graph showing the melting curve distribution of seven microorganisms and an internal reference gene is shown in FIG. 1, and the graph showing the ROC curves for detection of seven microorganisms is shown in FIG. 2.

TABLE 8

Detection performances of vaginal microorganisms in 160 samples

| Type of vaginal microorganism | Sensitivity | Specificity | AUC area |
|---|---|---|---|
| *Lactobacillus crispatus* (LC) | 91.3% | 95% | 0.948 |
| *Lactobacillus gasseri* (LG) | 96.3% | 98.7% | 0.979 |
| *Lactobacillus jensenii* (LJ) | 92.5% | 93.7% | 0.936 |
| *Lactobacillus iners* (LI) | 91.3% | 97.5% | 0.955 |
| *Gardnerella vaginalis* (GV) | 93.8% | 88.7% | 0.93 |
| *Candida albicans* (CA) | 91.3% | 91.2% | 0.917 |
| *Trichomonas vaginalis* (TV) | 91.3% | 92.5% | 0.906 |

Note: The above table shows the statistical results about sensitivity and specificity of the detected 80 positive and 80 negative samples calculated for each type of microorganism, with high accuracy.

Herein, specific examples are used to describe the inventive concept in detail, and the description of the above examples is only used to help understand the core idea of the present invention. It should be pointed out that for those of ordinary skill in the art, any obvious modification, equivalent replacement or other improvement made should be included in the protection scope of the present invention without departing from the inventive concept.

What is claimed is:

1. A primer-probe combination for vaginal microecosystem detection suitable for high-resolution melting curve analysis, comprising primers and probes for target gene detection against *Lactobacillus crispatus* (LC), *Lactobacillus gasseri* (LG), *Lactobacillus jensenii* (LJ), *Lactobacillus iners* (LI), *Gardnerella vaginalis* (GV), *Candida albicans* (CA) and *Trichomonas vaginalis* (TV), with nucleotide sequences shown below:

*Lactobacillus crispatus* detection primer LC-F: SEQ ID NO: 1,
*Lactobacillus crispatus* detection primer LC-R: SEQ ID NO: 2,
*Lactobacillus crispatus* detection probe LC-FP: SEQ ID NO: 3;
*Lactobacillus gasseri* detection primer LG-F: SEQ ID NO: 4,
*Lactobacillus gasseri* detection primer LG-R: SEQ ID NO: 5,
*Lactobacillus gasseri* detection probe LG-FP: SEQ ID NO: 6;
*Lactobacillus jensenii* detection primer LJ-F: SEQ ID NO: 7,
*Lactobacillus jensenii* detection primer LJ-R: SEQ ID NO: 8,
*Lactobacillus jensenii* detection probe LJ-FP: SEQ ID NO: 9;
*Lactobacillus iners* detection primer LI-F: SEQ ID NO: 10,
*Lactobacillus iners* detection primer LI-R: SEQ ID NO: 11,
*Lactobacillus iners* detection probe LI-FP: SEQ ID NO: 12;
*Gardnerella vaginalis* detection primer GV-F: SEQ ID NO: 13,
*Gardnerella vaginalis* detection primer GV-R: SEQ ID NO: 14,
*Gardnerella vaginalis* detection probe GV-FP: SEQ ID NO: 15;
*Candida albicans* detection primer CA-F: SEQ ID NO: 16,
*Candida albicans* detection primer CA-R: SEQ ID NO: 17,
*Candida albicans* detection probe CA-FP: SEQ ID NO: 18; and
*Trichomonas vaginalis* detection primer TV-F: SEQ ID NO: 19,
*Trichomonas vaginalis* detection primer TV-R: SEQ ID NO: 20,

*Trichomonas vaginalis* detection probe TV-FP: SEQ ID NO: 21;
   wherein the nucleotide sequences of the probes are labeled with fluorophores at the 5' end and quenching groups at the 3' end.

2. The primer-probe combination according to claim 1, further comprising primers and probes for detection of an internal reference gene GAPDH, with nucleotide sequences shown below:
   GAPDH detection primers: SEQ ID NOs: 22-23, and
   GAPDH detection probe: SEQ ID NO: 24;
   wherein the GAPDH detection probe is labeled with a fluorophore at the 5' end and a quenching group at the 3' end, and the fluorophore is different from that labeled at the 5' end of the probes for target gene detection.

3. A kit for vaginal microecosystem detection,
   comprising the primer-probe combination according to claim 1.

4. The kit according to claim 3, further comprising a PCR reaction solution, wherein each one-person-portion of the PCR reaction solution is composed of 0.5-1 μL of Taq DNA polymerase multi-amplified at a concentration of 1 U/μL, 1-5 μL of dNTPs at a concentration of 10 mM, 2-5 μL of $Mg^{2+}$ at a concentration of 5 mM, 2.5 μL of 10×DNA polymerase buffer and purified water making up to 15 μL.

5. The kit according to claim 3, further comprising a cell lysis reagent.

* * * * *

SEQUENCE LISTING

```
Sequence total quantity: 32
SEQ ID NO: 1             moltype = DNA   length = 24
FEATURE                  Location/Qualifiers
source                   1..24
                         mol_type = other DNA
                         organism = synthetic construct
modified_base            8
                         mod_base = OTHER
                         note = Locked nucleic acid thymine
modified_base            9
                         mod_base = OTHER
                         note = Locked nucleic acid adenosine
modified_base            10
                         mod_base = OTHER
                         note = Locked nucleic acid adenosine
modified_base            11
                         mod_base = OTHER
                         note = Locked nucleic acid thymine
SEQUENCE: 1
ctttcggtaa tgacgttagg aaag                                              24

SEQ ID NO: 2             moltype = DNA   length = 23
FEATURE                  Location/Qualifiers
source                   1..23
                         mol_type = other DNA
                         organism = synthetic construct
modified_base            10
                         mod_base = OTHER
                         note = Locked nucleic acid thymine
modified_base            11
                         mod_base = OTHER
                         note = Locked nucleic acid cytosine
modified_base            12
                         mod_base = OTHER
                         note = Locked nucleic acid thymine
modified_base            13
                         mod_base = OTHER
                         note = Locked nucleic acid thymine
SEQUENCE: 2
aatacgcttt cttatccggt att                                               23

SEQ ID NO: 3             moltype = DNA   length = 18
FEATURE                  Location/Qualifiers
source                   1..18
                         mol_type = other DNA
                         organism = synthetic construct
modified_base            1
                         mod_base = OTHER
                         note = Carboxyfluorescein cytosine
modified_base            3
                         mod_base = OTHER
                         note = Locked nucleic acid guanosine
modified_base            11
                         mod_base = OTHER
                         note = Locked nucleic acid guanosine
modified_base            18
                         mod_base = OTHER
                         note = Adenosine minor groove binder
SEQUENCE: 3
cggcggatgg gtgagtaa                                                     18
```

```
SEQ ID NO: 4              moltype = DNA  length = 19
FEATURE                   Location/Qualifiers
source                    1..19
                          mol_type = other DNA
                          organism = synthetic construct
modified_base             5
                          mod_base = OTHER
                          note = Locked nucleic acid thymine
modified_base             7
                          mod_base = OTHER
                          note = Locked nucleic acid adenosine
modified_base             8
                          mod_base = OTHER
                          note = Locked nucleic acid cytosine
modified_base             10
                          mod_base = OTHER
                          note = Locked nucleic acid thymine
SEQUENCE: 4
gtgttgacct gggctacac                                                      19

SEQ ID NO: 5              moltype = DNA  length = 19
FEATURE                   Location/Qualifiers
source                    1..19
                          mol_type = other DNA
                          organism = synthetic construct
modified_base             5
                          mod_base = OTHER
                          note = Locked nucleic acid cytosine
modified_base             12
                          mod_base = OTHER
                          note = Locked nucleic acid cytosine
SEQUENCE: 5
ccttccagct tcgtgtagg                                                      19

SEQ ID NO: 6              moltype = DNA  length = 16
FEATURE                   Location/Qualifiers
source                    1..16
                          mol_type = other DNA
                          organism = synthetic construct
modified_base             1
                          mod_base = OTHER
                          note = Carboxyfluorescein thymine
modified_base             4
                          mod_base = OTHER
                          note = Locked nucleic acid adenosine
modified_base             7
                          mod_base = OTHER
                          note = Locked nucleic acid guanosine
modified_base             10
                          mod_base = OTHER
                          note = Locked nucleic acid cytosine
modified_base             16
                          mod_base = OTHER
                          note = Guanosine minor groove binder
SEQUENCE: 6
tggacggtac aacgag                                                         16

SEQ ID NO: 7              moltype = DNA  length = 26
FEATURE                   Location/Qualifiers
source                    1..26
                          mol_type = other DNA
                          organism = synthetic construct
modified_base             14
                          mod_base = OTHER
                          note = Locked nucleic acid adenosine
modified_base             15
                          mod_base = OTHER
                          note = Locked nucleic acid guanosine
SEQUENCE: 7
gaaaccacct aagagattag gttttc                                              26

SEQ ID NO: 8              moltype = DNA  length = 24
FEATURE                   Location/Qualifiers
source                    1..24
                          mol_type = other DNA
                          organism = synthetic construct
modified_base             10
                          mod_base = OTHER
                          note = Locked nucleic acid cytosine
```

```
SEQUENCE: 8
cagcgagtgc ccaacttaat gctg                                            24

SEQ ID NO: 9              moltype = DNA  length = 21
FEATURE                   Location/Qualifiers
source                    1..21
                          mol_type = other DNA
                          organism = synthetic construct
modified_base             1
                          mod_base = OTHER
                          note = Carboxyfluorescein cytosine
modified_base             3
                          mod_base = OTHER
                          note = Locked nucleic acid guanosine
modified_base             4
                          mod_base = OTHER
                          note = Locked nucleic acid guanosine
modified_base             6
                          mod_base = OTHER
                          note = Locked nucleic acid adenosine
modified_base             9
                          mod_base = OTHER
                          note = Locked nucleic acid adenosine
modified_base             10
                          mod_base = OTHER
                          note = Locked nucleic acid adenosine
modified_base             21
                          mod_base = OTHER
                          note = Guanosine minor groove binder
SEQUENCE: 9
cggggacaaa gagacaggtg g                                               21

SEQ ID NO: 10             moltype = DNA  length = 21
FEATURE                   Location/Qualifiers
source                    1..21
                          mol_type = other DNA
                          organism = synthetic construct
modified_base             9
                          mod_base = OTHER
                          note = Locked nucleic acid guanosine
modified_base             12
                          mod_base = OTHER
                          note = Locked nucleic acid thymine
SEQUENCE: 10
ccctgcgtga gtgaagaagg g                                               21

SEQ ID NO: 11             moltype = DNA  length = 19
FEATURE                   Location/Qualifiers
source                    1..19
                          mol_type = other DNA
                          organism = synthetic construct
modified_base             9
                          mod_base = OTHER
                          note = Locked nucleic acid adenosine
modified_base             11
                          mod_base = OTHER
                          note = Locked nucleic acid cytosine
SEQUENCE: 11
gcagtattac cgcggctgc                                                  19

SEQ ID NO: 12             moltype = DNA  length = 21
FEATURE                   Location/Qualifiers
source                    1..21
                          mol_type = other DNA
                          organism = synthetic construct
modified_base             1
                          mod_base = OTHER
                          note = Carboxyfluorescein guanosine
modified_base             5
                          mod_base = OTHER
                          note = Locked nucleic acid thymine
modified_base             7
                          mod_base = OTHER
                          note = Locked nucleic acid thymine
modified_base             8
                          mod_base = OTHER
                          note = Locked nucleic acid thymine
modified_base             10
                          mod_base = OTHER
```

```
                                note = Locked nucleic acid thymine
modified_base                   11
                                mod_base = OTHER
                                note = Locked nucleic acid thymine
modified_base                   12
                                mod_base = OTHER
                                note = Locked nucleic acid guanosine
modified_base                   21
                                mod_base = OTHER
                                note = Guanosine minor groove binder
SEQUENCE: 12
gctctgttgt tggtgaagaa g                                                   21

SEQ ID NO: 13                   moltype = DNA   length = 21
FEATURE                         Location/Qualifiers
source                          1..21
                                mol_type = other DNA
                                organism = synthetic construct
modified_base                   8
                                mod_base = OTHER
                                note = Locked nucleic acid thymine
modified_base                   10
                                mod_base = OTHER
                                note = Locked nucleic acid guanosine
SEQUENCE: 13
gccacggttg gtgagagtgg c                                                   21

SEQ ID NO: 14                   moltype = DNA   length = 19
FEATURE                         Location/Qualifiers
source                          1..19
                                mol_type = other DNA
                                organism = synthetic construct
modified_base                   10
                                mod_base = OTHER
                                note = Locked nucleic acid adenosine
modified_base                   11
                                mod_base = OTHER
                                note = Locked nucleic acid guanosine
modified_base                   12
                                mod_base = OTHER
                                note = Locked nucleic acid thymine
modified_base                   13
                                mod_base = OTHER
                                note = Locked nucleic acid thymine
SEQUENCE: 14
tgctcgtcaa gttggagca                                                      19

SEQ ID NO: 15                   moltype = DNA   length = 14
FEATURE                         Location/Qualifiers
source                          1..14
                                mol_type = other DNA
                                organism = synthetic construct
modified_base                   1
                                mod_base = OTHER
                                note = Carboxyfluorescein thymine
modified_base                   4
                                mod_base = OTHER
                                note = Locked nucleic acid guanosine
modified_base                   14
                                mod_base = OTHER
                                note = Thymine minor groove binder
SEQUENCE: 15
tgcgtgacca acct                                                           14

SEQ ID NO: 16                   moltype = DNA   length = 19
FEATURE                         Location/Qualifiers
source                          1..19
                                mol_type = other DNA
                                organism = synthetic construct
modified_base                   8
                                mod_base = OTHER
                                note = Locked nucleic acid guanosine
modified_base                   11
                                mod_base = OTHER
                                note = Locked nucleic acid adenosine
SEQUENCE: 16
ccgctaggtg aacctgcgg                                                      19

SEQ ID NO: 17                   moltype = DNA   length = 21
```

```
FEATURE                    Location/Qualifiers
source                     1..21
                           mol_type = other DNA
                           organism = synthetic construct
modified_base              6
                           mod_base = OTHER
                           note = Locked nucleic acid adenosine
modified_base              9
                           mod_base = OTHER
                           note = Locked nucleic acid guanosine
modified_base              11
                           mod_base = OTHER
                           note = Locked nucleic acid adenosine
SEQUENCE: 17
gaaccaaagc aagtttgttt c                                              21

SEQ ID NO: 18              moltype = DNA   length = 11
FEATURE                    Location/Qualifiers
source                     1..11
                           mol_type = other DNA
                           organism = synthetic construct
modified_base              1
                           mod_base = OTHER
                           note = Carboxyfluorescein Locked nucleic acid adenosine
modified_base              3
                           mod_base = OTHER
                           note = Locked nucleic acid thymine
modified_base              4
                           mod_base = OTHER
                           note = Locked nucleic acid guanosine
modified_base              5
                           mod_base = OTHER
                           note = Locked nucleic acid adenosine
modified_base              8
                           mod_base = OTHER
                           note = Locked nucleic acid thymine
modified_base              11
                           mod_base = OTHER
                           note = Thymine minor groove binder
SEQUENCE: 18
actgatttgg t                                                         11

SEQ ID NO: 19              moltype = DNA   length = 20
FEATURE                    Location/Qualifiers
source                     1..20
                           mol_type = other DNA
                           organism = synthetic construct
modified_base              5
                           mod_base = OTHER
                           note = Locked nucleic acid guanosine
modified_base              6
                           mod_base = OTHER
                           note = Locked nucleic acid cytosine
SEQUENCE: 19
gagggccaca tgaatgactc                                                20

SEQ ID NO: 20              moltype = DNA   length = 21
FEATURE                    Location/Qualifiers
source                     1..21
                           mol_type = other DNA
                           organism = synthetic construct
modified_base              6
                           mod_base = OTHER
                           note = Locked nucleic acid guanosine
modified_base              8
                           mod_base = OTHER
                           note = Locked nucleic acid guanosine
modified_base              11
                           mod_base = OTHER
                           note = Locked nucleic acid adenosine
SEQUENCE: 20
ggggtgagat agatctaccc c                                              21

SEQ ID NO: 21              moltype = DNA   length = 14
FEATURE                    Location/Qualifiers
source                     1..14
                           mol_type = other DNA
                           organism = synthetic construct
modified_base              1
```

```
                        mod_base = OTHER
                        note = Carboxyfluorescein cytosine
modified_base           2
                        mod_base = OTHER
                        note = Locked nucleic acid adenosine
modified_base           4
                        mod_base = OTHER
                        note = Locked nucleic acid thymine
modified_base           6
                        mod_base = OTHER
                        note = Locked nucleic acid thymine
modified_base           8
                        mod_base = OTHER
                        note = Locked nucleic acid adenosine
modified_base           11
                        mod_base = OTHER
                        note = Locked nucleic acid thymine
modified_base           14
                        mod_base = OTHER
                        note = Thymine minor groove binder
SEQUENCE: 21
cagtatgaag tctt                                                        14

SEQ ID NO: 22           moltype = DNA   length = 19
FEATURE                 Location/Qualifiers
source                  1..19
                        mol_type = other DNA
                        organism = synthetic construct
SEQUENCE: 22
aagggtgcag ctgagctag                                                   19

SEQ ID NO: 23           moltype = DNA   length = 19
FEATURE                 Location/Qualifiers
source                  1..19
                        mol_type = other DNA
                        organism = synthetic construct
SEQUENCE: 23
gcacaagctt tgtacatgg                                                   19

SEQ ID NO: 24           moltype = DNA   length = 22
FEATURE                 Location/Qualifiers
source                  1..22
                        mol_type = other DNA
                        organism = synthetic construct
modified_base           1
                        mod_base = OTHER
                        note = Hexane cytosine
modified_base           22
                        mod_base = OTHER
                        note = Cytosine Black hole quencher-1
SEQUENCE: 24
cagcaagcat tcctggggtg gc                                               22

SEQ ID NO: 25           moltype = DNA   length = 110
FEATURE                 Location/Qualifiers
source                  1..110
                        mol_type = unassigned DNA
                        organism = Lactobacillus crispatus
SEQUENCE: 25
ggtaatgacg ttaggaaagc gagcggcgga tgggtgagta acacgtgggg aacctgcccc      60
atagtctggg ataccacttg gaaacaggtg ctaataccgg ataagaaagc                 110

SEQ ID NO: 26           moltype = DNA   length = 126
FEATURE                 Location/Qualifiers
source                  1..126
                        mol_type = unassigned DNA
                        organism = Lactobacillus gasseri
SEQUENCE: 26
tgacctgggc tacacacgtg ctacaatgga cggtacaacg agaagcgaac ctgcgaaggc      60
aagcggatct ctgaaagccg ttctcagttc ggactgtagg ctgcaactcg cctacacgaa     120
gctgga                                                                 126

SEQ ID NO: 27           moltype = DNA   length = 144
FEATURE                 Location/Qualifiers
source                  1..144
                        mol_type = unassigned DNA
                        organism = Lactobacillus jensenii
SEQUENCE: 27
ccacctaaga gattaggttt tcccttcggg gacaaagaga caggtggtgc atggctgtcg      60
```

```
tcagctcgtg tcgtgagatg ttgggttaag tcccgcaacg agcgcaaccc ttgttaatag  120
ttgccagcat taagttgggc actc                                         144

SEQ ID NO: 28           moltype = DNA  length = 135
FEATURE                 Location/Qualifiers
source                  1..135
                        mol_type = unassigned DNA
                        organism = Lactobacillus iners
SEQUENCE: 28
gcgtgagtga agaagggttt cggctcgtaa agctctgttg ttggtgaaga aggacagggg  60
tagtaactga cctttgtttg acggtaatca attagaaagt cacggctaac tacgtgccag  120
cagccgcggt aatac                                                   135

SEQ ID NO: 29           moltype = DNA  length = 105
FEATURE                 Location/Qualifiers
source                  1..105
                        mol_type = unassigned DNA
                        organism = Gardnerella vaginalis
SEQUENCE: 29
ggttggtgag agtggcgaac gggtgagtaa tgcgtgacca acctgcccca tgctccagaa  60
tagctcttgg aaacgggtgg taatgctgga tgctccaact tgacg                  105

SEQ ID NO: 30           moltype = DNA  length = 80
FEATURE                 Location/Qualifiers
source                  1..80
                        mol_type = unassigned DNA
                        organism = Candida albicans
SEQUENCE: 30
taggtgaacc tgcggaagga tcattactga tttggtgaat tgcaccacat gtgtttttct  60
ttgaaacaaa cttgctttgg                                              80

SEQ ID NO: 31           moltype = DNA  length = 89
FEATURE                 Location/Qualifiers
source                  1..89
                        mol_type = unassigned DNA
                        organism = Trichomonas vaginalis
SEQUENCE: 31
ggccacatga atgactcagc gcagtatgaa gtctttgttt cttccgaaa acaagctcaa   60
tgagagccat cggggtaga tctatctca                                     89

SEQ ID NO: 32           moltype = DNA  length = 82
FEATURE                 Location/Qualifiers
source                  1..82
                        mol_type = other DNA
                        organism = synthetic construct
SEQUENCE: 32
aagggtgcag ctgagctagg cagcagcaag cattcctggg gtggcatagt ggggtggtga  60
ataccatgta caaagcttgt gc                                           82
```